(12) United States Patent
Jensen et al.

(10) Patent No.: US 6,921,775 B2
(45) Date of Patent: Jul. 26, 2005

(54) METHODS FOR MODULATING BRAIN DAMAGE

(75) Inventors: Frances E. Jensen, Chestnut Hill, MA (US); Joseph Volpe, Brookline, MA (US); Paul Rosenberg, Newton, MA (US); Pamela L. Follett, Boxboro, MA (US)

(73) Assignee: Children's Medical Center Corporation, Boston, MA (US)

( * ) Notice: Subject to any disclaimer, the term of this patent is extended or adjusted under 35 U.S.C. 154(b) by 95 days.

(21) Appl. No.: 10/213,393

(22) Filed: Aug. 5, 2002

(65) Prior Publication Data

US 2003/0092730 A1 May 15, 2003

Related U.S. Application Data

(63) Continuation-in-part of application No. 10/121,892, filed on Apr. 12, 2002, now abandoned, which is a continuation-in-part of application No. 09/922,564, filed on Aug. 3, 2001, now abandoned.

(51) Int. Cl.[7] ............................................... A61K 31/35
(52) U.S. Cl. ........................................ 514/455; 514/25
(58) Field of Search ............................. 514/25, 455, 45

(56) References Cited

U.S. PATENT DOCUMENTS

| | | | |
|---|---|---|---|
| 5,438,130 A | 8/1995 | Goldin et al. | ............ 536/27.81 |
| 5,506,231 A | 4/1996 | Lipton | ........................ 514/289 |
| 6,495,601 B1 * | 12/2002 | Hochman | .................... 514/562 |

OTHER PUBLICATIONS

Pellock et al., Mental Retardation and Developmental Disabilities Research Reviews (2000) 6/4 (309–323) (abstract).*

* cited by examiner

*Primary Examiner*—Phyllis G. Spivack
(74) *Attorney, Agent, or Firm*—Ivor R. Elrifi; Nicholas P. Triano, III; Mintz, Levin, Cohn, Ferris, Glovsky and Popeo, P.C.

(57) ABSTRACT

Methods are disclosed for modulating brain damage mediated by non-NMDA ionotropic glutamate receptor antagonists, as topiramate, in conditions such as periventricular leukomalacia, cerebral palsy, mental retardation and neonatal stroke.

5 Claims, 12 Drawing Sheets

METHODS FOR MODULATING BRAIN DAMAGE

RELATED APPLICATIONS

The present application is a Continuation-In-Part application of and claims priority from U.S. Continuation patent application Ser. No. 10/121,892, filed on Apr. 12, 2002 now abandoned, and from U.S. patent application Ser. No. 09/922,564, filed on Aug. 3, 2001 now abandoned. All of the above applications are expressly incorporated by reference.

BACKGROUND OF THE INVENTION

Preterm infants, particularly those of low birth weight and gestational age, often present neurodevelopmental deficits which include global cognitive delay, cerebral palsy, blindness, and deafness. Deficits such as cognitive delay and cerebral palsy may be attributed, at least in part, to hypoxic/ischemic damage in white and/or grey matter of the brain.

A common example of white matter injury observed in infants as a complication of premature birth is referred to as periventricular leukomalacia (PVL). PVL is the principal neuropathological correlate of cerebral palsy. The lesion is defined by focal necrosis of the deep periventricular white matter involving all cellular components, combined with a more diffuse white matter injury that appears selective for developing oligodendrocytes (OLs) (Gilles and Averill (1977) *Ann. Neurol.* 2:49–56; Dambska et al. (1989) *J. Child Neurol.* 4:291–298; and Rorke (1998) In Pathology of Perinatal Brain Injury New York: Raven). Reduced cerebral myelin is the most prominent subsequent cerebral abnormality observed in premature infants with evidence of PVL in the neonatal period (Paneth et al. (1990) *J. Pediatr.* 116:975–984; Rorke (1992) *Brain Pathol.* 2:211–221; Iida et al. (1995) *Pediatr. Neurol.* 13:296–304; Olsen et al. (1997) *Ann. Neurol.* 41:754–761; Skranes et al. (1997) *Neuropediatrics* 28:149–154; and Inder et al. (1999) *Ann Neurol.* 46:755–760).

A propensity to cerebral ischemia caused by impaired cerebrovascular autoregulation, combined with a selective vulnerability of immature OLs to ischemic injury (Volpe (1997) *Brain Dev.* 19:519–534), may contribute to the prevalence of this lesion in the preterm infant. Developing OLs in vitro have been demonstrated to be more vulnerable than are mature, myelin basic protein (MBP)-expressing OLs to oxidative stress (Back et al. (1998) *J. Neurosci.* 18:6241–6253) and to glutamate receptor (GluR)-mediated ischemic death (Fern and Moller (2000) *J. Neurosci.* 20:34–42). OLs appear to be more vulnerable than are other glia when exposed to hypoxia/hypoglycemia in vitro (Lyons and Kettenmann (1998) *J. Creb. Blood Flow Metab.* 18:521–530). Furthermore, a number of in vivo studies have demonstrated selective white matter injury after experimental hypoxia/ischemia in the rat brain during early postnatal development (Rice et al. (1981) *Ann. Neurol.* 9:131–134; Towfighi et al. (1991) *Acta Neuropathol.* 81:578–587; Sheldon et al. (1996) *Biol. Neonate* 69:327–341; Yue et al. (1997) *Neuropathol. Appl. Neurobiol.* 23:16–25; Ikeda et al. (1998) *Am. J. Obstet. Gynecol.* 178:24–32; Reddy et al. (1998) *Pediadr. Res.* 43:674–682; and Matsuda et al. (1999) *Am. J. Obstet. Gynecol.* 181:725–730).

Both clinical and experimental studies indicate that hypoxia/ischemia is a major underlying cause of PVL. Experimental models of ischemia in immature animals implicate glutamate as a critical factor in the pathogenesis of brain injury. Hypoxic/ischemic conditions result in elevated cerebral glutamate levels in the immature rat brain, measured by in vivo microdialysis (Benveniste et al. (1984) *J. Neurochem.* 4:1369–1374; Silverstein et al. (1991) *Pediatr. Res.* 30:587–590). Clinical relevance of the experimental studies is suggested by the demonstration of elevated glutamate in the CSF of term infants after perinatal hypoxia/ischemia (Hagberg (1992) *Biol. Neonate* 66:205–213). Glutamate has been shown to be toxic to oligodendroglia in vivo and in vitro by receptor-independent (Oka et al. (1993) *J. Neurosci.* 13:1441–1453; Yoshioka et al. (1996) *J. Neurochem.* 64:2442–2448; and Back et al. (1998) *J. Neurosci.* 18:6241–6253) and receptor-mediated mechanisms (Yoshioka et al. (1995) *J. Neurochem.* 64:2442–2448; Yoshioka et al. (1996) *J. Neurosci. Res.* 46:427–438; Matute et al. (1997) *Proc. Natl. Acad. Sci. U.S.A.* 94:8830–8835; McDonald et al. (1998) *Nat. Med.* 4:291–297; and Pitt et al. (2000) *Nat. Med.* 6:67–70). OLs express functional GluRs in vitro, and these are exclusively of the non-NMDA subtype (Gallo et al. (1994) *Glia* 11:94–101; Patneau et al. (1994) *Neuron* 12:357–371).

SUMMARY OF THE INVENTION

The present invention provides methods and compositions for modulating brain damage mediated by non-NMDA ionotropic glutamate receptors, particularly in fetal and neonatal brains. The invention is based, at least in part, on the discovery that hypoxia/ischemia-mediated brain injury is attenuated by the non-NMDA ionotropic glutamate receptor antagonists NBQX and topiramate. As a consequence of this inhibition, physical markers of brain damage such as white matter lesions, oligodendrocyte cell death, and myelin basic protein loss are decreased. These effects are attributable, at least in part, to excitotoxic oligodendrocyte injury mediated by nonNMDA ionotropic glutamate receptors. Inhibition of non-NMDA glutamate receptors is thought to prevent injury following hypoxic/ischemic insult by preventing the influx of glutamate, an excitatory amino acid which mediates neuronal cell death.

Accordingly, in one aspect, the present invention is directed to a method for modulating, e.g., inhibiting, glutamate-mediated neuronal cell death by modulating non-NMDA ionotropic glutamate receptors. The method includes treating a subject with a non-NMDA ionotropic glutamate receptor antagonist, such that disorders associated with glutamate-mediated neuronal cell death are treated.

In one aspect, the invention provides methods for treating periventricular leukomalacia (PVL), mental retardation, and/or neonatal stroke in a subject (e.g., a mammal, such as a human). The method further includes administering a non-NMDA ionotropic glutamate receptor antagonist and a pharmaceutically acceptable carrier to treat these conditions. The method includes antagonists such as 2,3-Dioxo-6-nitro-1,2,3,4-tetrahydrobenzo[f]quinoxaline-7-sulphonamide (NBQX), topiramate, 1-(4aminophemyl)-4-methyl-7,8-methylene-dioxy-5H-2,3-benzodiazepine) (GYKI52466), kynurenic acid, 6-cyano-7nitroquinoxaline-2,3-dione (CNQX), LY377770, decahydroisoquinoline (LY293558), 6,7-Dinitroquinoxaline-2,3 -dione (DNQX), ASAP 187, 1-(4'-Aminophenyl)-3,5-dihydro-7,8-dimethoxy-4H-2,3-benzodiazepin-4-one (CFM-2), and γ-Glutamylaminomethyl sulphonic acid (GAMS), or pharmaceutically acceptable salts thereof (e.g., NBQX disodium salt and CNQX disodium salt). In a preferred embodiment, the antagonist is NBQX. In another preferred embodiment, the antagonist is topiramate. The method further provides treating periventricular leukomalacia (PVL), mental retardation, and/or stroke in a neonate. The method still further provides treating periventricular leukomalacia (PVL), mental retardation, and/or stroke in a fetus by administering the antagonist to a pregnant mother.

In another aspect, the invention features a method for preventing one or more causes of cerebral palsy in a subject (e.g., a human). The method includes administering a non-NMDA ionotropic glutamate receptor antagonist and a pharmaceutically acceptable carrier to prevent cerebral palsy. The method further includes antagonists such as NBQX, topiramate, GYKI52466, kynurenic acid, CNQX, LY377770, LY293558, DNQX, ASAP 187, CFM-2, and GAMS, or pharmaceutically acceptable salts thereof (e.g., NBQX disodium salt and CNQX disodium salt). In another preferred embodiment, the antagonist is topiramate. The method further provides preventing one or more causes of cerebral palsy in a neonate. The method still further provides preventing one or more causes of cerebral palsy in a fetus by administering the antagonist to a pregnant mother.

In yet another aspect, the invention features a method for treating grey and/or white matter injury in the brain of a perinatal subject. The method includes administering a non-NMDA ionotropic glutamate receptor antagonist and a pharmaceutically acceptable carrier to treat grey and/or white matter injury. The method further includes antagonists such as NBQX, topiramate, GYKI52466, kynurenic acid, CNQX, LY377770, LY293558, DNQX, ASAP 187, CFM-2, and GAMS, or pharmaceutically acceptable salts thereof (e.g., NBQX disodium salt and CNQX disodium salt). In a preferred embodiment, the antagonist is NBQX. In another preferred embodiment, the antagonist is topiramate. The method further provides preventing one or more causes of cerebral palsy in a neonate. The method still further provides preventing one or more causes of cerebral palsy in a fetus by administering the antagonist to a pregnant mother.

The invention further provides a method for identifying a compound capable of treating PVL, mental retardation, and/or stroke using a postnatal day seven (P7) rat pup. The method includes administering to a p7 rat, having been inflicted with hypoxic/ischemic injury, a test compound and assaying the ability of the test compound to modulate neonatal white matter injury.

In another aspect, the invention provides a method for identifying a compound capable of preventing one or more causes of cerebral palsy using a postnatal day seven (P7) rat pup. The method includes administering to a p7 rat, having been inflicted with hypoxic/ischemic injury, a test compound and assaying the ability of the test compound to modulate neonatal white matter injury.

Kits which include a pharmaceutical composition comprising a non-NMDA ionotropic glutamate receptor antagonist and a pharmaceutically acceptable carrier packed with instructions for use are also provided by the invention. In one embodiment, the kit is used to treat PVL, mental retardation, and/or neonatal stroke. In another embodiment, the kit is used to treat one or more causes of cerebral palsy. In still another embodiment, the kit is used to treat fetal grey and/or white matter injury in the brain. In yet another aspect, the pharmaceutical composition may be administered to a neonate or to a fetus via a pregnant mother. The kits include antagonists such as NBQX, topiramate, GYKI52466, kynurenic acid, CNQX, LY377770, LY293558, DNQX, ASAP 187, CFM-2, and GAMS, or pharmaceutically acceptable salts thereof (e.g., NBQX disodium salt and CNQX disodium salt).

BRIEF DESCRIPTION OF THE DRAWINGS

FIG. 2A depicts injury after injection with 5 mol AMPA plus 5 nmol MK-801. FIG. 2B depicts the effect of AMPA on rats of different ages.

FIGS. 4A and 4B depict dose response curves demonstrating protection of topiramate against kainate excitotoxicity (4A) and OGD induced cell death (4B) in a culture model of OL precursors. FIG. 4C depicts a dose response to topiramate in vivo, demonstrating attenuation of MBP injury at P11 with systemic topiramate treatment following hypoxia/ischemia at P7. FIGS. 4D and 4E depict that a loss of MBP is seen in the P11 pup ipsilateral to a carotid ligation (4D), following UCL/hypoxia at P7, and as compared to the contralateral side (4E). FIGS. 4F and 4G demonstrate that systemic post-treatment with effective doses of topiramate attenuate this injury (4F, ipsilateral; 4G, contralateral). FIG. 4H depicts hematoxilyn and eosin stain of the P11 pup ipsilateral to a carotid ligation (4D), demonstrating the region of MBP staining, present under relatively spared cortex.

FIG. 5A depicts a graph evaluating control cultures exposed to either NBQX or topiramate for 24 hours, which shows no significant difference in BrdU incorporation or cell number. However, sister cultures do show significant difference in BrdU incorporation when exposed to growth factors PDGF and bFGF. Immunocytochemical assessment with OL stage specific markers for O4, O1 and MBP confirm no maturational difference between NBQX-treated, topiramate-treated and untreated sister cultures. FIG. 5B depicts graphs evaluating pups treated with doses of topiramate or NBQX effective for injury prevention, which show no significant difference in number of O4 cells in subcortical white matter of the corpus callosum and external capsule that demonstrate BrdU incorporation (5D) than untreated littermates. FIG. 5C illustrates ICC analysis with O4, O1 and MBP stage specific OL markers in NBQX-treated pups, topiramate-treated pups (right panels) and untreated littermates (left panels) show no qualitative difference in maturation. FIG. 5D demonstrates high power image of BrdU labeling (red) with O4 (green); the overlayed image depicts high power image of O1 (red) and bisbenzamide, demonstrating immature OLs.

FIG. 6A depicts a graph showing that topiramate and NBQX blocks kainate- or OGD-evoked calcium accumulation in OL precursor cells in culture. NBQX blocks kainate-induced and OGD-induced calcium uptake to basal levels ($p<0.001$). Topiramate partially blocks kainate-induced calcium uptake but completely blocks OGD-induced calcium uptake ($p<0.001$). FIGS. 6B–6G demonstrate that topiramate and NBQX block calcium uptake via AMPA/kainate receptors in sub-cortical white matter. FIG. 6B demonstrates that kainate evokes cobalt uptake in white matter of P7 rats, in cells identified by ICC as O4+ OLs (square, shown at high power (6C) and O4 labeled (6D)). FIG. 6C shows that NBQX blocks cobalt uptake in the white matter of adjacent slices. FIG. 6E illustrates that topiramate blocks cobalt uptake in the white matter of adjacent slices. FIG. 6F demonstrate immunolabeling for O4+ pre-OLs of same section demonstrates topiramate blocks cobalt uptake in OL precursors.

Figure 1A:
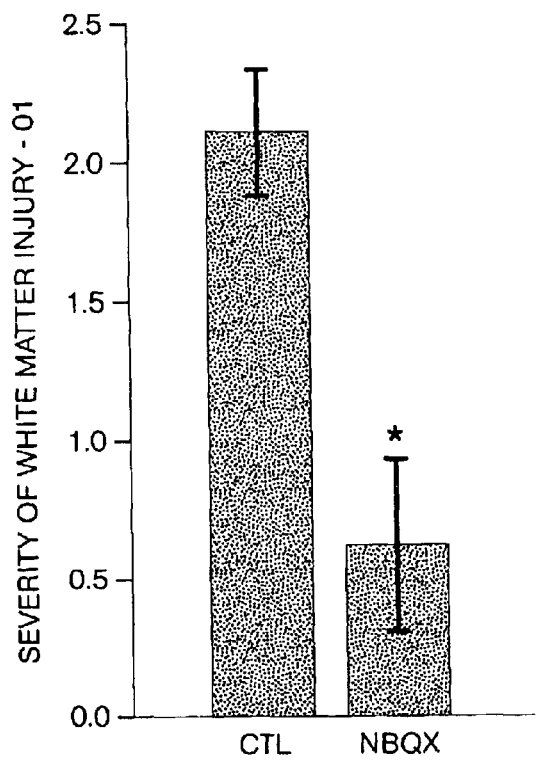
FIGS. 1A–1B depict graphs evaluating white matter injury with the oligodendrocyte (OL)-specific markers O1 (FIG. 1A) and myelin basic protein (MBP) (FIG. 1B). Comparison of the severity of white matter injury 96 hours after hypoxia/ischemia was performed at P7 (perinatal day seven) in treated (n=7) and untreated (n=9) pups.

Other features and advantages of the invention will be apparent from the following detailed description, and from the claims.

DETAILED DESCRIPTION

The present invention provides methods and compositions for modulating brain damage mediated by non-NMDA ionotropic glutamate receptors, in particular in fetal and neonatal brains. The invention is based, at least in part, on the discovery that hypoxia/ischemia-mediated injury is attenuated by the non-NMDA ionotropic glutamate receptor antagonists NBQX and topiramate. As a consequence of this inhibition, white matter lesions, oligodendrocyte cell death, and myelin basic protein loss is decreased. These effects are attributable, at least in part, to excitotoxic oligodendrocyte injury mediated by non-NMDA ionotropic glutamate receptors.

Accordingly, in one aspect, the present invention is directed to a method for modulating, e.g., inhibiting, glutamate-mediated neuronal cell death by modulating non-NMDA ionotropic glutamate receptors. The method includes administering to a subject a non-NMDA ionotropic glutamate receptor antagonist in order to treat PVL, mental retardation, neonatal stroke, fetal grey matter injury, and/or fetal white matter injury, as well as to prevent one or more causes of cerebral palsy.

Definitions

In one aspect, the invention features a method for treating a subject (e.g., a mammal, such as a human) suffering or prone to suffering from a condition characterized by PVL, mental retardation, neonatal stroke, one or more causes of cerebral palsy, fetal grey matter injury, and/or fetal white matter injury. The method includes administering to the subject a non-NMDA ionotropic glutamate receptor antagonist, thereby treating the subject.

As used herein, the term "non-NMDA ionotropic glutamate receptor antagonist" includes any compound which has the ability to modulate, e.g., decrease, the amount (e.g., concentration or level) or stability of glutamate activity in a cell, or to modulate, e.g., stimulate or inhibit, the pharmacological activity of glutamate in a cell, such as a central nervous system cell (e.g., an oligodendrocyte and/or MBP). Non-NMDA ionotropic glutamate receptor antagonists act at the level of the non-NMDA ionotropic glutamate receptor in the signaling pathway that leads to neural cytotoxicity. The term non-NMDA ionotropic glutamate receptor antagonist includes AMPA antagonists, kainate antagonists, and AMPA/kainate antagonists. Non-NMDA ionotropic glutamate receptor antagonists of the invention are compounds which inhibit ionotropic glutamate receptor production, activity or stability, and include compounds such as NBQX, NBQX disodium salt, topiramate, GYKI52466, kynurenic acid, CNQX, CNQX disodium salt, LY377770, LY293558, DNQX, ASAP 187, CFM-2, and GAMS. Other ionotropic glutamate receptor antagonists known in the art are incorporated herein by reference.

The terms "disorders associated with neuronal cell death", "disorders associated with hypoxia/ischemia", and "disorders associated with hypoxic/ischemic damage" include disorders characterized by injury and/or death to white matter cells and/or grey matter cells. Such disorders include, but are not limited to PVL, cerebral palsy, mental retardation, stroke, and epilepsy.

The terms "neonate" and "neonatal" are intended to refer to babies up to one year old. Preferably, such babies are preterm babies. As used herein, the term "preterm" is intended to refer to a baby born at a gestational age of less than 266 days.

The terms "fetus" and "fetal" are intended to refer to a developing human from approximately three months after conception to birth.

The term "perinatal" is intended to refer to the period shortly before and after birth, art defined as beginning with completion of the twentieth to twenty eighth week of gestation and ending 7 to 28 days after birth.

The term "pregnant mother" is intended to refer to a mammal (e.g., a human) which contains unborn young within the body.

The term "PVL" is intended to refer to damage and softening of the white matter, the inner portion of the brain that transmits information between the nerve cells and the spinal cord, as well as from one part of the brain to another. This type of injury is characterized by focal necrosis with a loss of all cellular elements deep in the periventricular white matter, and diffuse white matter involvement characterized by injury to glial cells which are thought to be oligodendrocyte precursors.

The term "mental retardation" is intended to refer to sub-average intellectual ability that is equivalent to or less than an IQ of 70, is present from birth or infancy, and is manifested especially by abnormal development, by learning difficulties, and by problems in social adjustment. Mental retardation is often observed in preterm infants, particularly those of low birth weight and gestational age.

The term "neonatal stroke" is intended to refer to sudden diminution or loss of consciousness, sensation, and voluntary motion caused by rupture or obstruction (as by a clot) of an artery of the brain which occurs in a baby up to one year old.

The term "cerebral palsy" is intended to refer to a disability resulting from damage to the brain before, during, or shortly after birth and outwardly manifested by muscular incoordination and speech disturbances. Cerebral palsy is caused by damage to one or more specific areas of the brain during development. The causes of cerebral palsy are diverse and include genetic, metabolic, infectious, traumatic, endocrine, and hypoxic/ischemic disorders. As used herein, the terms "hypoxic" and "hypoxia" refer to a deficiency of oxygen reaching the tissues of the body. The terms "ischemic" and "ischemia", as used herein, refer to localized tissue anemia due to obstruction of the inflow of arterial blood.

The terms "grey matter injury" and "white matter injury" are intended to refer to injury to the grey or white matter of the brain. Such injury includes injury to brain cells (e.g., white matter injury) and brain cell death (e.g., white matter cell death and myclin basic protein loss). As used herein, "grey matter" refers to neural tissue of the brain that contains cell bodies as well as nerve fibers, has a brownish gray color, and forms most of the cortex and nuclei of the brain. As used herein, "white matter" refers to neural tissue that consists largely of myclinated nerve fibers, has a whitish color, and underlies the gray matter of the brain.

As used herein, the language "treating" is intended to include methods of bringing a non-NMDA ionotropic glutamate receptor antagonist into proximity with white and/or grey matter (e.g., an oligodendrocyte), such that the antagonist can modulate glutamate-mediated excitotoxicity in the white and/or grey matter. The term "excitotoxicity" is art recognized and is intended to refer to increased levels of excitatory amino acids which are toxic to neurons. This may occur when protective mechanisms are inhibited by ischemia or inflammation.

As used herein, the term "subject" is intended to include animals susceptible to conditions characterized by excitotoxicity in the brain, preferably mammals, most preferably humans. In a preferred embodiment, the subject is a primate. In an even more preferred embodiment, the primate is a human. In another preferred embodiment, the subject is a neonate or a fetus. Other examples of subjects include dogs, cats, goats, and cows.

Various aspects of the invention are described in further detail in the following subsections:

Pharmaceutically Acceptable Formulations

Pharmaceutical compositions, and packaged formulations, comprising a composition of the invention (e.g., a non-NMDA ionotropic glutamate receptor antagonist) and a pharmaceutically acceptable carrier are also provided by the invention. In the method of the invention, the non-NMDA ionotropic glutamate receptor antagonist can be administered in a pharmaceutically acceptable formulation. Such pharmaceutically acceptable formulation typically includes the non-NMDA ionotropic glutamate receptor antagonist as well as a pharmaceutically acceptable carrier(s) and/or excipient(s). As used herein, "pharmaceutically acceptable carrier" includes any and all solvents, dispersion media, coatings, antibacterial and antifungal agents, isotonic and absorption delaying agents, and the like that are physiologically compatible. Excipients include pharmaceutically acceptable stabilizers and disintegrants. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Preferably, the route of administration is oral. Solutions or suspensions used for parenteral, intradetmal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a non-NMDA ionotropic glutamate receptor antagonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch orlactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical formulation, used in the method of the invention, contains a therapeutically effective amount of the non-NMDA ionotropic glutamate receptor antagonist. A "therapeutically effective amount" refers to an amount effective, at dosages and for periods of time necessary, to achieve the desired result. A therapeutically effective amount of the non-NMDA ionotropic glutamate receptor antagonist may vary according to factors such as the disease state, age, and weight of the subject, and the ability of the non-NMDA ionotropic glutamate receptor antagonist (alone or in combination with one or more other agents) to elicit a desired response in the subject. Dosage regimens may be adjusted to provide the optimum therapeutic response. A therapeutically effective amount is also one in which any toxic or detrimental effects of the non-NMDA ionotropic glutamate receptor antagonist are outweighed by the therapeutically beneficial effects. A non-limiting dosage range (i.e., an effective dosage) is from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

It is to be noted that dosage values may vary with the severity of the condition to be alleviated. It is to be further understood that for any particular subject, specific dosage regimens should be adjusted over time according to the individual need and the professional judgment of the person administering or supervising the administration of the non-NMDA ionotropic glutamate receptor antagonist and that dosage ranges set forth herein are exemplary only and are not intended to limit the scope or practice of the claimed invention.

The invention, in another embodiment, provides a pharmaceutical composition consisting essentially of a non-NMDA ionotropic glutamate receptor antagonist and a pharmaceutically acceptable carrier, as well as methods of use thereof to modulate disorders associated with neuronal cell death e.g., PVL, mental retardation, neonatal stroke, cerebral palsy, fetal grey matter injury, and/or fetal white matter injury with the composition. By the term "consisting essentially of" it is meant that the pharmaceutical composition does not contain any other modulators of non-NMDA ionotropic glutamate receptors. In one embodiment, the pharmaceutical composition of the invention can be provided as a packaged formulation. The packaged formulation may include a pharmaceutical composition of the invention in a container and printed instructions for administration of the composition for treating a subject having a disorder associated with a non-NMDA ionotropic glutamate receptor, e.g., disorders associated with neuronal cell death. The instructions may include directions for the treatment of adults and/or children. Preferably, the instructions include directions for the treatment of neonates. In another preferred embodiment, the instructions include directions for the treatment of a fetus via the administration of the composition to the pregnant mother.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Screening Assays

The ability of a non-NMDA ionotrophic glutamate receptor antagonist to produce a neurosalutary effect in a subject may be determined using any of a variety of art known assays. For example, the ability of a non-NMDA ionotrophic glutamate receptor antagonist to prevent cell damage, death, and/or function after an injury, e.g., an hypoxic/ischemic injury, may be determined histologically (e.g., by assaying tissue loss, immature OL loss, or MBP expression as set forth in the examples below).

Other tests that may be used to determine the ability of a non-NMDA ionotrophic glutamate receptor antagonist to produce a neurosalutary effect in a subject include standard tests of neurological function in human subjects or in animal models of brain injury such as memory tests (e.g., Morris water maze, T maze, spontaneous alternation test, and bar-pressing task); locomotor activity (e.g., vertical movements, sniffing, grooming, coordination, and spontaneous locomotor activity); exploratory activity (e.g., novel large cage test); anxiety (e.g., freezing test, hole-board test, elevated plus maze, forced swimming test); nociception (e.g., hot plate test); feeding motivation; and aggressive behavior. Examples of such tests can be found in Miyachi et al. (1994) *Neurosci. Lett.* 175:92–94; Vaillend et al. (1995) *Behav. Genet.* 25:569–579; Fiore et al. (1996) *Exp. Parasitol.* 83:46–54; Valentinuzzi et al. (1998) *Learning & Memory* 5:391–403; Andreatini et al. (1999) *Braz. J. Med. Biol. Res.* 32:1121–1126; Crabbe et al. (1999) *Science* 284:1670–1672; Rao et al. (1999) *Psychopharm.* 144:61–66; and U.S. Pat. No. 5,447,939 (1995).

Animal models suitable for use in the assays of the present invention include the immature rat model of hypoxia/ischemia (described in Follett et al. (2000) *J. Neurosci.* 20:9235–9241, set forth in Example 1). This animal model tests how well a compound can enhance the survival and sprouting of OL and MBP after hypoxic/ischemic injury. Accordingly, after administration of the non-NMDA ionotrophic glutamate receptor antagonist, the brains of these animals may be examined for cell damage and/or death. Alternatively, these animals may be evaluated for recovery of a certain function, e.g., the assays discussed supra.

The invention is further illustrated by the following examples, which should not be construed as further limiting. The contents of all references, patents and published patent applications cited throughout this application, as well as the Figures are hereby incorporated by reference.

EXAMPLE 1

NBQX-Mediated Inhibition of White Matter Injury

The methods used in this example are described in Follett et al. (2000) *J. Neurosci.* 20:9235–9241, incorporated by reference herein.

The purpose of this example was to examine in vivo the contribution of GluR-mediated toxicity to the selective loss of immature OLs in age-dependent cerebral white matter injury. First, the sensitivity of immature white matter to experimental hypoxia/ischemia at the age when the cerebral white matter of a rat is primarily populated by immature OLs was evaluated. To establish whether this injury was involved in GluR activation, the presence of AMPA GluRs on the vulnerable cells was confirmed and the protective efficacy of treatment with the non-NMDA antagonist 6-nitro-7-sulfamoylbenzo(f)quinoxaline-2,3-dione (NBQX) was subsequently assessed. Furthermore, the white matter selectivity and age-dependent nature of the GluR-mediated injury was assayed with glutamate agonist injections at different ages.

Selective Vulnerability of Immature White Matter to Hypoxic Ischemia

Immunocytochemistry revealed little MBP expression in rat pups before P7. A progressive increase between P7 and P18 indicated that white matter is predominantly populated with immature OLs at P7. Because the white matter of premature infants at high risk for hypoxic/ischemic white matter injury is also populated with immature OLs (Kinney and Back, 1998), this age was chosen to deliver the hypoxic/ischemic insult. Unilateral carotid ligation followed by hypoxia (6% $O_2$ for one hour) at P7 resulted in a reproducible and regionally specific injury in the periventricular and subcortical white matter. Injury was limited to the white matter without evidence of injury to cortical neurons. Histological observation at 48 hours after hypoxia/ischemia demonstrated numerous ISEL positively stained cells within the subcortical white matter ipsilateral to the ligation, but not within ipsilateral overlying cortex. Immunostaining of sections from rats killed 96 hr after hypoxia/ischemia demonstrated diminished expression of the O1 marker for immature OLs in seven of nine rats in subcortical white matter ipsilateral to the carotid ligation when compared with expression in the contralateral hemisphere. Ipsilateral injury included the loss of MBP expression in the OL processes extending into the cortex and decreased thickness of the periventricular white matter and external capsule in four of nine rats. All rats showed an ipsilateral decrease in the presence of MBP in the OL processes extending into the cortex. In summary, hypoxic/ischemic injury at P7 resulted in selective white matter injury as demonstrated by the loss of MBP expression in OL processes 96 hours later.

Presence of AMPA-Preferring GluRs in OLs at P7

Because of the potential role of glutamate in hypoxic/ischemic white matter injury and the presence of AMPA-preferring GluRs on OLs in vitro, whether AMPA-preferring receptors were present on immature OLs at this age in vivo was evaluated. Immunocytochemical analysis using AMPA receptor subunit antibodies demonstrated robust expression of the GluR4 subunit in white matter at P7 (n=4). Immunocytochemistry with the O1 antibody to detect immature OLs (the primary OL stage present at P7) and the GluR4 antibody demonstrated widespread double-labeling in the corpus callosum, pericallosal white matter, and external and internal capsule. In contrast, little coexpression of GluR4 was detected in the predominant OL stages seen at younger (P4; O4+ O1−) and older (P11; MBP+) ages. These data confirm the relative high expression of AMPA receptors in immature OLs in cerebral white matter at this vulnerable age.

Systemic NBQX Attenuated Hypoxic/Ischemic White Matter Injury

Figure 1B:
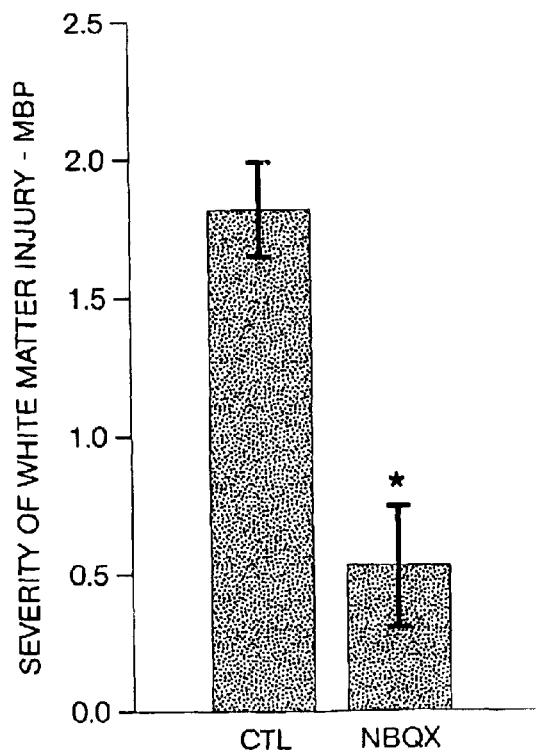

Because of the presence of AMPA receptors on immature OLs during the time period of susceptibility to hypoxia/ischemia, whether AMPA receptor blockade with NBQX would attenuate the injury was examined. Pups treated with NBQX (n=7) at the termination of the period of hypoxia after carotid ligation show a marked attenuation of the ipsilateral decrease in O1 and MBP staining observed 96 hours after the insult when compared with untreated littermate controls (n=9). A semiquantitative analysis of lesion severity demonstrated significant attenuation of white matter injury in rats post-treated with NBQX, compared with vehicle-treated controls, when evaluated for either O1 expression ($p<0.005$) or MBP expression ($p<0.001$) (set forth in FIG. 1). Treated pups showed either no detectable injury (three of seven pups) or mild ipsilateral injury, generally limited to slight loss of MBP or O1 expression in the cortical processes.

Systemic NBQX Attenuated AMPA-Mediated White Matter Injury

Figure 2A:
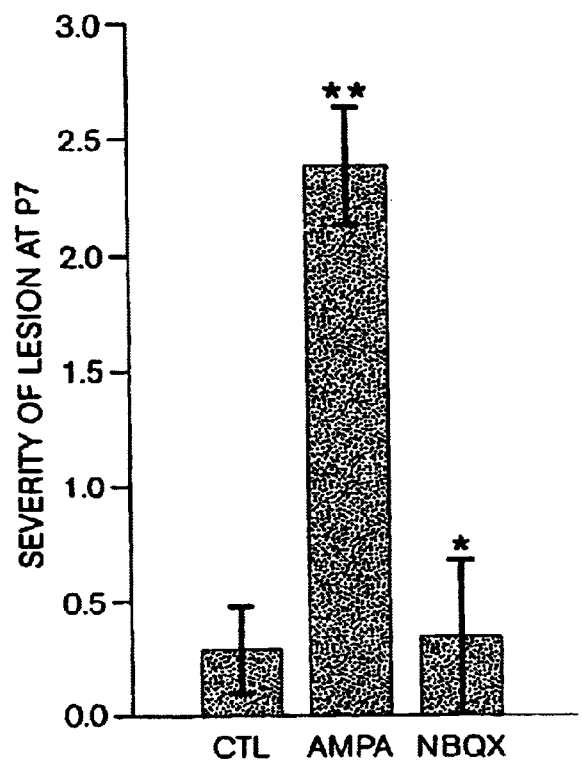
FIGS. 2A–2B depict graphs evaluating white matter injury after intracerebral injections of AMPA.

NBQX attenuation of the selective white matter injury after hypoxia/ischemia implicated GluR-mediated toxicity as an important mechanism of injury in immature OLs. To confirm a relationship between the activation of AMPA receptors in cerebral white matter and the vulnerability to injury, AMPA was injected directly into immature white matter. Intracerebral injections of 5 nmol of AMPA plus 5 nmol of MK-801 produced white matter injury in P7 rat pups (n=8) in the absence of significant cortical or hippocampal injury. Most P7 rats demonstrated areas of hypercellularity surrounding tissue disruption and necrosis in the pericallosal white matter, frequently with hemorrhage and with little cortical injury. Minimal to no injury was present in vehicle-injected controls (M K801 alone; n=7) at the same age (t test, $p<0.001$). The severity of white matter injury was evaluated by the size of the resulting lesion (set forth in FIG. 2). Staining with ISEL showed evidence of cell death in the white matter of the pericallosal region at P7 in rats injected with AMPA and of injury limited to the site of the needle track in controls. Systemic administration of the AMPA receptor antagonist NBQX significantly attenuated white matter injury at P7 (FIG. 2A, t test, $p<0.005$). These results indicate a receptor-mediated mechanism of injury from AMPA injections and confirm the efficacy of systemic NBQX, administered as a post-treatment.

Age-Dependent Vulnerability of Cerebral White Matter to AMPA

Figure 2B:
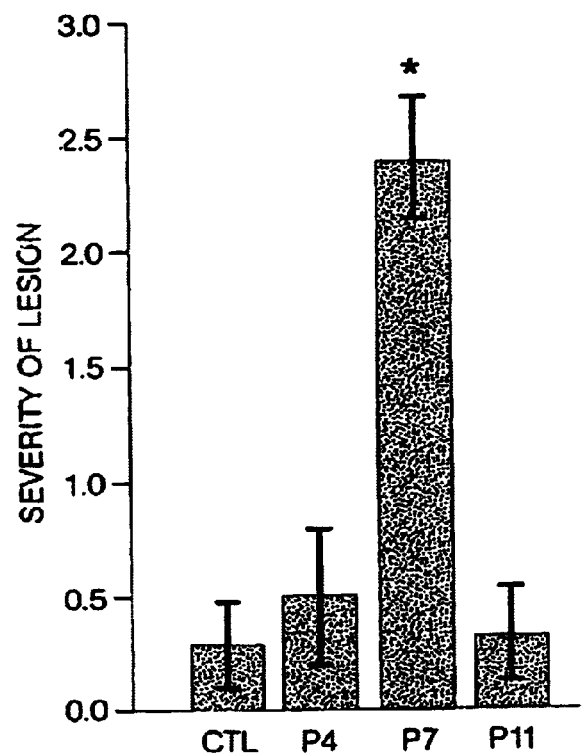

To determine whether AMPA toxicity was age dependent, lesion size after intracerebral AMPA injections at P4, P7, and P11 was compared. Injections at both P4 (n=4) and P11 (n=6) produced significantly less white matter injury than did injections at P7 (one-way ANOVA, $p<0.001$). Comparison of the resulting white matter injury is demonstrated by a histogram of the pericallosal lesion size (FIG. 2B). Whereas pups injected at P4 had minimal cortical injury, animals injected at P11 exhibited widespread injury in the overlying cortex and adjacent hippocampus. These results indicated that intracerebral injections of AMPA produce an in vivo white matter lesion in an age-dependent manner, the most severe and specific lesion is at P7, and less severe and less specific lesions are at both younger (P4) and older (P11) ages.

Discussion

This example indicated that the age-dependent vulnerability of OLs to hypoxic/ischemic injury may be mediated by GluR activation and may be correlated with maturational differences in GluR expression. An increased vulnerability of white matter to hypoxic/ischemic injury at P7 was demonstrated, a maturational stage when white matter is populated with immature OLs. The presence of AMPA-preferring GluR subunits on the immature OLs at this age in vivo was confirmed. After hypoxia/ischemia at P7, systemic treatment with the AMPA receptor antagonist NBQX significantly attenuated the selective white matter injury. Furthermore, the vulnerability of white matter to intracerebral injections of AMPA appeared to be age dependent, with the greatest susceptibility to injury at P7. Hypoxic/ischemic- and AMPA-induced injury are each blocked by NBQX, indicating that the toxicity is receptor mediated. These results indicate that GluR-mediated toxicity is a contributing factor in the age-dependent, selective injury to developing OLs after hypoxia/ischemia in the immature brain.

The progressive development and differentiation of oligodendrocytes from progenitors to mature, myelinating oligodendrocytes has been well characterized both in vitro (Gard and Pfeiffer, 1990; Asou et al., 1995) and in vivo (LeVine and Goldman, 1988; Hardy and Reynolds, 1991, 1997). Similar developmental sequences of OL maturation are observed in the white matter of the rat and human (Kinney and Back, 1998), further supporting the use of the rat as an experimental model of PVL. Expression of MBP does not begin until P7, and this expression is followed by a rapid increase in myelin over the following few days. Therefore, this developmental stage correlates with a time in premature infants when white matter is highly vulnerable to injury.

GluR expression also appears to be maturation dependent. The presence of AMPA-preferring GluRs on OLs is well established (Gallo et al., 1994; Meucci et al., 1996; Matute et al., 1997), and the variable expression of AMPA receptor subtypes in different brain regions during development has been demonstrated by in situ hybridization (Pellegrini-Giampietro et al., 1991). In agreement with these results, relatively high levels of expression of AMPA receptors on immature OLs in vivo at P7, in areas vulnerable to hypoxic/ischemic injury were demonstrated. This age is before the time in development when expression rapidly increases in the cortex (Pellegrini-Giampietro et al., 1991; Petralia and Wenthold, 1992). The presence of GluRs on immature OLs, at an age when there is a comparative lack of expression in the cortex, may explain the relatively specific vulnerability of white matter at this maturational stage to GluR-mediated toxicity.

Moderate hypoxia/ischemia in P7 rats resulted in a selective white matter injury with relative cortical sparing. The proportion of cortical injury after hypoxia/ischemia varies with age; white matter injury is more common after cerebral hypoxia/ischemia in immature rats, whereas cortical and subcortical gray matter infarction is typically seen in the adult (Rice et al., 1981; Andine et al., 1990; Sheldon et al., 1996; Uehara et al., 1999). In addition, selective white matter injury attributable to AMPA injections is age-dependent. Intracerebral AMPA caused the most selective and severe white matter injury at P7, with younger ages less prone to injury and older ages more susceptible to neuronal injury. White matter injury was not observed with MK-801 injections at P7, confirming that this was not a mechanical injury. Therefore, there is an age-dependent injury to white matter resulting from either hypoxia/ischemia or GluR agonist injections.

The AMPA antagonist NBQX was effective at attenuating immature white matter injury in vivo, caused either by direct receptor activation or by hypoxia/ischemia. NBQX blocked the injury at P7 caused by AMPA injections, consistent with the results of others (Yoshioka et al., 1996; McDonald et al., 1998) and suggesting a receptor-mediated cause of injury. However, in addition to blocking activation of non-NMDA receptors, NBQX has been demonstrated to induce a protective hypothermia (Young et al., 1983; Nurse and Corbett, 1996). No difference in rectal temperatures between the treated and untreated groups was observed, consistent with reports of others (Hagberg et al., 1994). A protective effect of hypothermia in P7 rats is significant only if present during hypoxia (Yager et al., 1993), and in the current example, NBQX treatment was initiated after hypoxia. The presence of GluRs in the vulnerable cells and the attenuation of hypoxic/ischemic white matter injury with AM PA receptor blockade together implicate receptor-mediated excitotoxicity as a contributing factor in hypoxic/ischemic white matter injury in the immature brain.

The in vivo efficacy of NBQX is consistent with previous studies demonstrating attenuation of GluR-mediated excitotoxicity in vitro (Yoshioka et al., 1995, 1996; Matute et al., 1997; McDonald et al., 1998; Pitt et al., 2000). In vitro, immature OLs appear to be more susceptible to excitotoxicity than are mature OLs (Fern and Moller, 2000), and the mechanism of excitotoxicity may be calcium dependent (David et al., 1996; Yoshioka et al., 1996; Brorson et al., 1999; Li and Stys, 2000). Neither the source of elevated glutamate nor the mechanism of cell death in vivo is known; however, reverse glutamate transport from axons (Li et al., 1999; Rossi et al., 2000) or glia (Fern and Moller, 2000) has been suggested as a source. The protective efficacy of non-NMDA receptor blockade supports the hypothesis that selective injury to immature OLs by a receptor-mediated mechanism is sufficient to cause cerebral white matter injury in vivo.

The results presented in this example indicate that developing white matter exhibits an age window of enhanced susceptibility to GluR-mediated excitotoxicity. Injury due to hypoxia/ischemia parallels that caused by direct AMPA toxicity, with maximum selective white matter injury at P7. Cerebral white matter at this age is populated primarily by immature OLs that possess AMPA receptor subunits. In agreement with the proposed vulnerability of immature OLs to excitotoxicity by a GluR-mediated mechanism, the AMPA receptor antagonist NBQX attenuated both the AMPA-induced lesions as well as the hypoxic/ischemic white matter injury. Taken together, these data indicate that hypoxic/ischemic injury in developing white matter is mediated at least in part by excitotoxicity via glutamate receptors on immature OLs.

EXAMPLE 2

Topiramate-Mediated Inhibition of White Matter Injury

Periventricular leukomalacia (PVL) is a principal pathology underlying cerebral palsy. Substantial evidence implicates ischemic white matter injury as an important cause of PVL. It has been previously demonstrated that hypoxia/ischemia in the immature rat brain leads to selective oligodendroglial (OL) injury during postnatal days five through seven (P 5–7). This selective white matter lesion can be blocked by systemic treatment with the non-NMDA ionotropic glutamate receptor antagonist NBQX, indicating a role for glutamate receptor-mediated toxicity in age dependent injury (set forth in Example 1). Topiramate is an FDA approved CNS drug shown to attenuate AMPA currents. Whether systemic administration of topiramate would similarly attenuate hypoxic/ischemic white matter injury in the immature rat model of PVL was addressed in this example.
Analysis of White Matter Cell Death P7 rat pups underwent unilateral carotid ligation followed by hypoxia (6% $O_2$ for one hour). Following hypoxia, littermates were treated with either topiramate (30 mg/kg, i.p., q12 h, 4 doses, n=12) or vehicle (n=12). 48 hours after hypoxia/ischemia, pups were evaluated with in situ end labeling (ISEL) for the presence of cell death in white matter. Briefly, coronal sections were labeled for the presence of single-stranded DNA fragments as a sensitive indicator of cell death. ISEL positive cells in white matter ipsilateral to the ligation in each of three coronal sections (at the level of the anterior hippocampus, mid-dorsal hippocampus, and posterior dorsal hippocampus) were counted and a mean was taken for each rat.

96 hours post-ischemia/hypoxia, pups were evaluated with ICC for loss of MBP expression ipsilateral to the ligation as compared to the contralateral side. Coronal sections were evaluated by immunocytochemistry with a monoclonal against MBP, and detected with fluorescent secondary antibody. Three sections were evaluated for each rat: the anterior hippocampus, the mid-dorsal hippocampus, and the posterior dorsal hippocampus. Lesion severity was assigned a value on a scale from 0 to 3 as follows: 0 if ipsilateral and colateral hemispheres were similar; 1 if ipsilateral loss was limited to cortical processes; 2, if loss of staining included thinning of the periventricular white matter; and 3 if white matter tracts included a full thickness loss of staining in the capsule. A mean severity score was obtained for immature and mature OL markers in each rat.
Topiramate Inhibition of White Matter Cell Death In vehicle treated control rats, there was consistent evidence of white matter cell death. Five out of six pups had greater than 20 ISEL positive cells per section in subcortical white matter, and three out of six pups had greater than 100 ISEL positive cells per section in subcortical white matter.

Figure 3A:
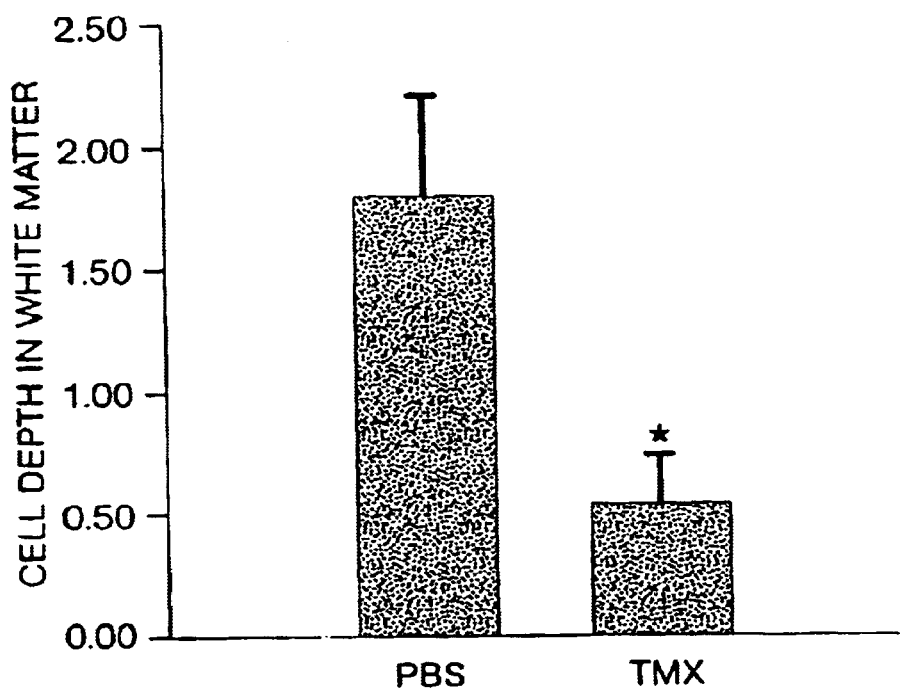
FIGS. 3A–3B depict graphs of white matter cell death (FIG. 3A) and MBP expression (FIG. 3B). In 3A, pups were sacrificed 48 hours after hypoxia/ischemia and were evaluated by in situ end labeling (ISEL) for the presence of white matter cell death. In 3B, pups were sacrificed 96 hours after hypoxia/ischemia and were evaluated for loss of MBP expression ipsilateral to the carotid ligation as compared to the contralateral side.
Figure 3B:
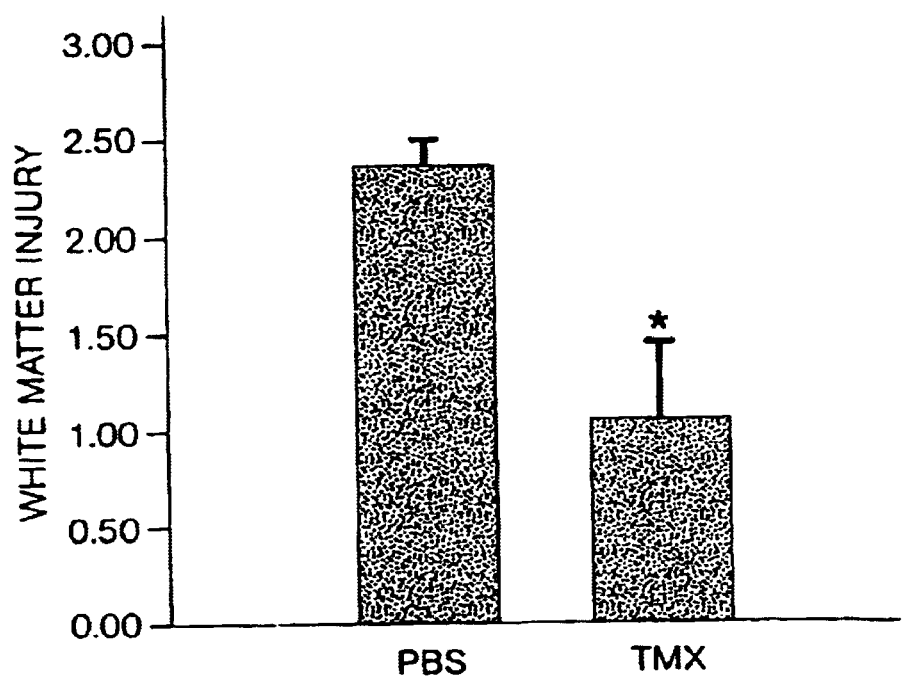

In topiramate treated rats, there were significant decreases in white matter cell death (p<0.03) (set forth in FIG. 3A). Five out of six pups treated with topiramate had less than 20 ISEL positive cells per section in subcortical white matter ipsilateral to the ligation.
Topiramate Inhibition of MBP Loss All vehicle treated control rats exhibited ipsilateral loss of MBP expression. Most rats had a severe decrease when a side by side comparison was performed In topiramate treated rats, there was significant attenuation of MBP loss (p=0.04) (set forth in FIG. 3B). None of the topiramate treated pups exhibited severe injury. Furthermore, two out of five pups treated with topiramate showed no appreciable loss of MBP expression ipsilateral to the carotid ligation.
Discussion Hypoxia/ischemia results in selective, age dependent glutamate receptormediated toxicity to immature oligodendrocytes in vivo. The systemic administration of the AMPA/kainate receptor antagonist NBQX following hypoxia/ischemia attenuates white matter injury. The data presented in this example indicate that systemic administration of topiramate following hypoxia/ischemia attenuated injury in a rat model of neonatal white matter injury. Thus, these results indicate that topiramate has clinical potential in the treatment of PVL, as well as other disorders involving white matter injury.

EXAMPLE 3

Use of Topiramate for the Treatment of Periventricular Leukomalacia

Materials and Methods
Subjects

Litters of male Long Evans rat pups (Charles River Laboratories, Wilmington, Mass.) were raised with dams in a temperature-controlled environment with 12 hour light-dark cycles. Pups underwent carotid ligation and hypoxia at post-natal-day (P)7. They were recovered on a thermal blanket at 33–34° C. (baseline temperature for P7 rats) and returned to their dam for 48–96 hours prior to sacrifice. Treated pups were given intra-peritoneal (i.p.) injections of 0.1 cc solutions of topiramate, NBQX or vehicle every 12 hours for 48 hours at P7 and P8 for treatment, control and normal development studies.

Effect of Topiramate on Normal White Matter Development

Oligodendrocyte maturation and myelin expression were evaluated in animals treated for 48 hours with topiramate as compared with normal development. The sub-cortical white matter was evaluated by immunocytochemistry with antibodies to O4, O1 and myelin basic protein (MBP), for changes in pre-myelinating OL populations and in the pattern of MBP expression in rats sacrificed at P9, acutely after treatment. To evaluate for any permanent effect on mature myelination, the quantity of MBP at P28 in animals treated for 48 hours at P7/8 with topiramate was compared with untreated littermates by Western blot.

Carotid Ligation with Hypoxia

Hypoxic/ischemic injury was generated in rats by unilateral carotid ligation followed by hypoxia (6% for 1 hour). It has been shown that this method produces selective white matter injury in P7 rats that can be significantly attenuated by blocking AMPA receptor activation (Follett et al., 2000). The methods used in this example are described in Follett et al (2000) *J. Neurosci.* 20:9235–9241, incorporated by reference herein.

Briefly, rats were anesthetized with ether and the proximal internal carotid artery was isolated from the sympathetic chain and ligated. Animals requiring prolonged sedation due to technical issues were removed from the study. The animals were recovered one hour, then placed in a sealed chamber infused with nitrogen to a level of 6% $O_2$, with body temperature maintained at 33–34° C. throughout. Body temperature was monitored by rectal probe at each stage and did not differ between treatment and control groups. Pups were allowed a 1–2 hour period of recovery after hypoxia then returned to their dam. Pups were randomized into treatment and control groups by weight to insure no size variation existed between the subjects and controls to start. Following hypoxia animals in the treatment group were given i.p. injections of topirmate (10, 30 or 50 mg/kg in 0.1 cc PBS) or equivalent volume of saline repeat treatment every 12 hours for 48 hours. Rats were sacrificed 96 hours after injection by perfusion with 4% paraformaldehyde, post-fixed for 1 hr, then cryoprotected in 30% sucrose in phosphate buffered saline (PBS).

Histological Analysis and Immunochemistry

Histological and immunocytochemical (ICC) analysis was carried out on serial 20–30 $\mu$m coronal sections, cut by either cryostat (for pre-mounted sections) or freezing microtome (floating sections) from the anterior extent of the lateral ventricles through the posterior extent of the dorsal hippocampus. Representative sections from all experimental animals were stained with hematoxylin and eosin (HE) for routine evaluation.

For ICC evaluation, adjacent mounted sections were incubated in 5–10% normal goat serum for one hour to block non-specific binding and concurrently permeabilized in 0.1% Triton X-100. Slides were incubated with MBP antibody (SMA-99, Sternberger Monoclonals, Baltimore, Md.) at a dilution of 1:800 in PBS with 1% normal goat serum plus 0.1% Triton overnight at 4° C., followed by Oregon Green (Molecular Probes, Eugene, Oreg.) anti-mouse IgG secondary antibody for one hour at room temperature. For detection of immature OLs, mounted sections were blocked in 10% normal goat serum for one hour, incubated overnight at 4° C. in either O4 or O1 monoclonal antibody at a dilution of 1:500 in PBS with 10% normal goat serum, rinse and incubated 1 hour in Alexa 594 anti-mouse IgM antibody (Molecular Probes, Eugene, Oreg.).

Assessment of Lesion Size and Statistical Analysis

Coronal sections stained with HE were assessed histologically for cortical injury by light microscopy. Adjacent serial sections were also stained with OL specific markers of immature and mature OLs, and used to compare the extent of white matter depletion following hypoxia/ischemia. Three adjacent pairs of coronal sections were evaluated for each rat, at the level of the anterior hippocampus, mid-dorsal hippocampus and posterior dorsal hippocampus by immunocytochemistry with OL specific antibodies for O1 and MBP. The white matter staining was compared ipsilateral and contralateral to the ligation and lesion severity was assigned a value on a scale of 0 to 3 as follows: 0 if the ipsilateral and contralateral hemispheres are similar; 1, change ipsilateral to the ligation is limited to a loss of staining in the cortical processes; 2, loss of staining included thinning of the periventricular white matter; 3, thinning of the white matter tracts included a full thickness loss of staining in the capsule. A mean severity score was obtained for immature and mature OL markers in each rat. Lesion severity for each marker was compared between the group treated with vehicle and the group treated with topiramate at each dose.

In vitro Slices

P6/7 Long Evans rat pups were sacrificed by decapitation and the brains were removed quickly and placed in ice cold rat ACSF. 300 $\mu$m coronal slices were cut on a live-slice dedicated vibratome while continually maintained in oxygen bubbled, cold ACSF. Slices were transferred to an oxygen chamber, where they were maintained at room temperature.

Cobalt Uptake

300 $\mu$m thick vibratome cut coronal slices were collected from the anterior commissure to the anterior aspect of the thalamus and placed in oxygen-rich ice cold rat ACSF. Stabilized slices were transferred to a room temperature oxygen chamber and maintained in ACSF. Stable slices were transferred to modified ACSF containing low calcium and 5 mM $CoCL_2$ and stimulated with 100 $\mu$M AMPA in the presence of 100 $\mu$M MK-801 and with or without topiramate in varying concentrations. Slices were incubated at room temperature for 20 minutes then rinsed in ACSF, followed by 3 rinses in ASCF containing 2 mM EDTA to chelate and remove any unbound cobalt. Cobalt was then precipitated with ammonium sulfate. Sections were fixed in 4% paraformaldehyde for 10 minutes, rinsed and stored in PBS. Silver enhancement of precipitate was carried out for improved visualization. Slices were transferred to enhancement solution (10% sucrose, 15.5 mM hydroquinone, 42 mM citric acid) and warmed to 50° C. Slices were moved to similar solution containing 0.1% silver nitrate, then incubated at 50° C. for 45 minutes, with solution changes every 15 minutes. Sections were rinsed in PBS then cryoprotected in 30% sucrose solution and 40 $\mu$m sections, cut using a freezing microtome, were mounted on slides and analyzed.

Culture and Treatment of Oligodendrocyte Precursor Cells

Primary oligodendrocyte precursor cells were isolated from mixed glial cultures of the forebrains of newborn Sprague-Dawley rats using a selective detachment procedure as described in detail elsewhere (McCarthy and de Vellis, 1980; Back et al., 1998), and further purified by differential adhesion (Back et al., 1998). Precursor cells were maintained in a chemically-defined medium (CDM) supplemented with recombinant human platelet derived growth factor-AA (PDGF, 10 ng/ml) and basic fibroblast growth factor (bFGF, 10 ng/ml). The CDM was Dulbecco Modified Eagle's Medium (DMEM) containing D-glucose (25 mM), L-glutamine (4 mM), sodium pyruvate (1 mM), human apo-transferrin (50 μg/ml), bovine pancreatic insulin (5 μg/ml), sodium selenium (30 nM), hydrocortisone (10 nM), D-biotin (10 nM), and bovine serum albumin (BSA, 1 mg/ml). All chemicals were from Sigma. Precursor cells were maintained in the presence of growth factors (PDGF+ bFGF) by refeeding with fresh medium every 48 hr for 7 days, to promote cell proliferation and prevent differentiation (Bogler et al., 1990). Experiments were performed with cultures maintained in CDM without the supplemental growth factors. These cultures were routinely characterized by immunochemical detection of cell-specific markers as described before (Back et al., 1998). Cultures at the beginning of experiments usually consisted of approximately 90% A2B5$^+$ oligodendrocyte precursors and less than 5% glial fibrillary acidic protein (GFAP)-positive astrocytes. Cells were plated on poly-DL-ornithine-coated 24-well plates for cell viability assays and on coated glass coverslips for immunocytochemistry, proliferation studies, and lineage analysis.

Kainic acid (Sigma-RBI) were first dissolved in 0.1N HCl, and cyclothiazide (Sigma) in 0.1N NaOH, then added to culture medium to the desired final concentration. The pH of the culture media was maintained at 7.4. Topiramate (RWJ Pharmaceutical Research Institute) and NBQX (Sigma-RBI) were directly dissolved in culture medium and applied 10 min prior to exposure of the cells to kainate or oxygen-glucose deprivation (OGD).

For OGD experiments, cultures were switched to the same medium that was deoxygenated and lacked glucose (Gibco). Topiramate or NBQX were directly dissolved in the glucose-free medium and applied 10 min prior to the onset of deoxygenation. Cultures were then transferred to an anaerobic chamber (Billups-Rothenberg, Inc., Del Mar, Calif.) at 37° C. Following OGD for 2 hr, D-glucose as a concentrated stock solution made in the glucose-free medium was added back to the cultures to a final concentration of 25 mM, and cultures were returned to a normoxic 5% CO2 incubator at 37° C.

Cell Viability Assay

Following exposure to kainate or OGD for 24 hr, cell death was quantitatively assessed using the trypan blue exclusion method (Perry et al., 1997). Cells in 5–7 adjacent fields (×200) per well were counted to determine cell survival. At least 1000 cells per condition were counted in control cultures. The mean±SEM values for each experimental group were obtained from at least three separate experiments, and each was performed in triplicate.

Immunocytochemical Studies and Cell Lineage Progression Analysis

Cell lineage progression was monitored by the sequential emergence of stage-specific immunochemical markers: A2B5, O4, O1, and MBP, as described previously (Back et al., 1998). Briefly, after blocking non-specific binding with 2% BSA and fixation with 2% paraformaldehyde, cells were incubated for 30 min with the primary antibodies (Chemicon): A2B5, O4, O1 and/or anti-MBP (each at 5 μg/ml), washed three times in PBS and incubated for another 30 min with tetramethylrhodamine isothiocyanate (TRITC)-conjugated goat anti-mouse IgM (1:50) for A2B5, O4, and O1, and fluorescein isothiocyanate (FITC)-conjugated goat anti-mouse IgG (1:50) for MBP. For the staining of the intracellular antigen, MBP, cells were first permeabilized with 0.2% Triton X-100 for 30 min. Cells were mounted in Flu6romount G (Southern Biotech Associates, Inc.) and viewed with a Zeiss epifluorescence microscope.

Cell Proliferation Studies

Cell proliferation was measured by determining the incorporation of the thymidine analog 5-bromo-2'-deoxyuridine (BrdU, 10 mM) into replicating DNA of cells during the last 2 hr of the experiment. Following the 2-hr pulse, cells were washed and stained with the surface antibody A2B5, as described above, and further fixed with ice-cold methanol for 10 min. The cells were subsequently treated with 2 N HCl for 10 min to denature nuclear DNA and 0.1 M sodium borate (pH 8.5) for 10 min to neutralize the acid. After the cells were incubated in a solution containing 2% BSA and 0.2% Triton X-100 for 30 min, BrdU incorporation was detected employing a murine monoclonal anti-BrdU antibody (Chemicon) and FITC-conjugated goat anti-mouse IgG. Quantitative analysis was performed by determining the percent of BrdU$^+$ cells in the A2B5$^+$ population. Data were presented as the mean±SEM of at least three independent experiments. All assays were performed in triplicate and at least 1000 cells counted for each data point.

$^{45}$Ca$^{2+}$Uptake

To assay Ca$^{2+}$ influx, cultures were incubated with $^{45}$CaCl$_2$ (8 μCi/ml) at room temperature for 10 min, then washed with Hank's balanced salts-solution (HBSS) and lysed with 1% Triton-X 100 in HBSS. Radioactivity in the whole lysate was counted by liquid scintillation.

Data Analysis

Statistical comparisons on the data of all experiments were performed using oneway analysis of variance (ANOVA), followed by Tukey post hoc analysis. Statistical significance was accepted for $p<0.05$.

Experimental Procedures

The purpose of this example was to examine whether the GluR antagonist potential of topiramate could be utilized for its potential therapeutic value against the excitotoxic component of age-dependent white matter injury relevant in PVL. First, a dose-dependent efficacy of topiramate in models of selective OL injury was established. Then, in order to asses the protective effect, an evaluation of whether an alteration in OL proliferation and maturation rate was contributing to the apparent protective effect was performed, as this would have important mechanistic as well as safety implications. Next, the models were assessed for evidence of calcium influx correlated with excitotoxicity. Finally, in order to demonstrate a potential for the relevance of these findings in the preterm infant, the presence of AMPA receptors was confirmed in human fetal parietal white matter during the window of vulnerability for PVL.

Figure 4A:
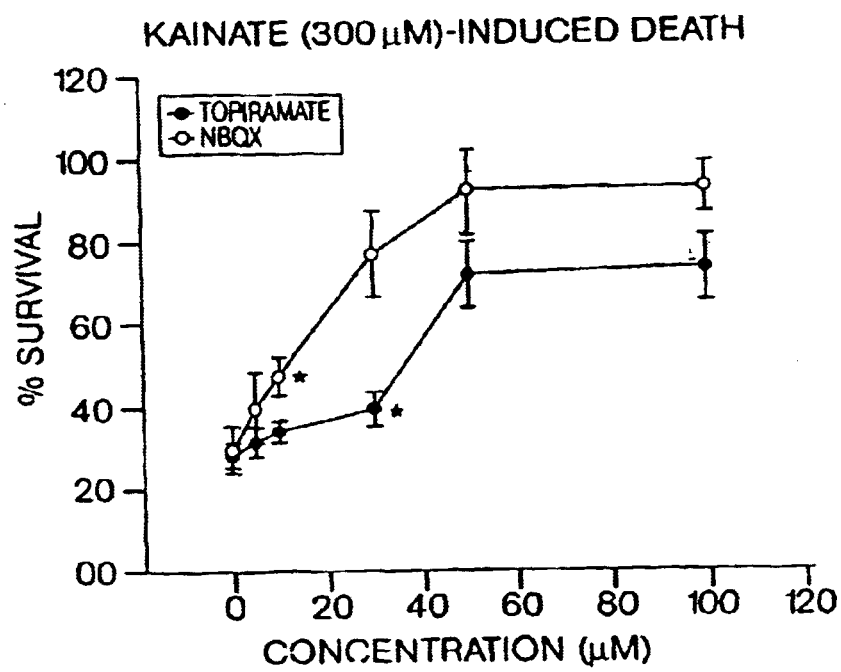
FIGS. 4A–4H demonstrate that topiramate protects against OGD induced pre-OL cell death and hypoxia/ischemia white matter injury.
Figure 4B:
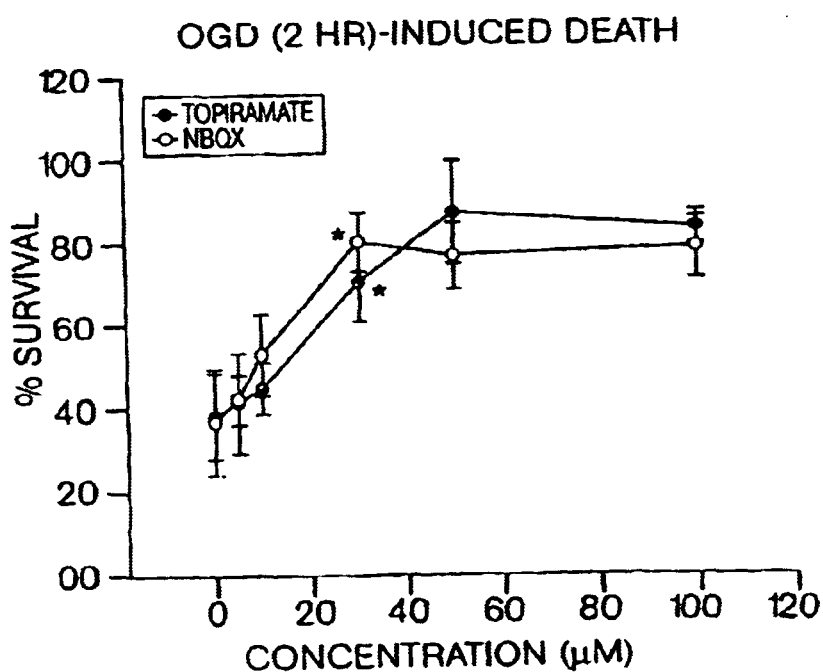
Figure 4C:
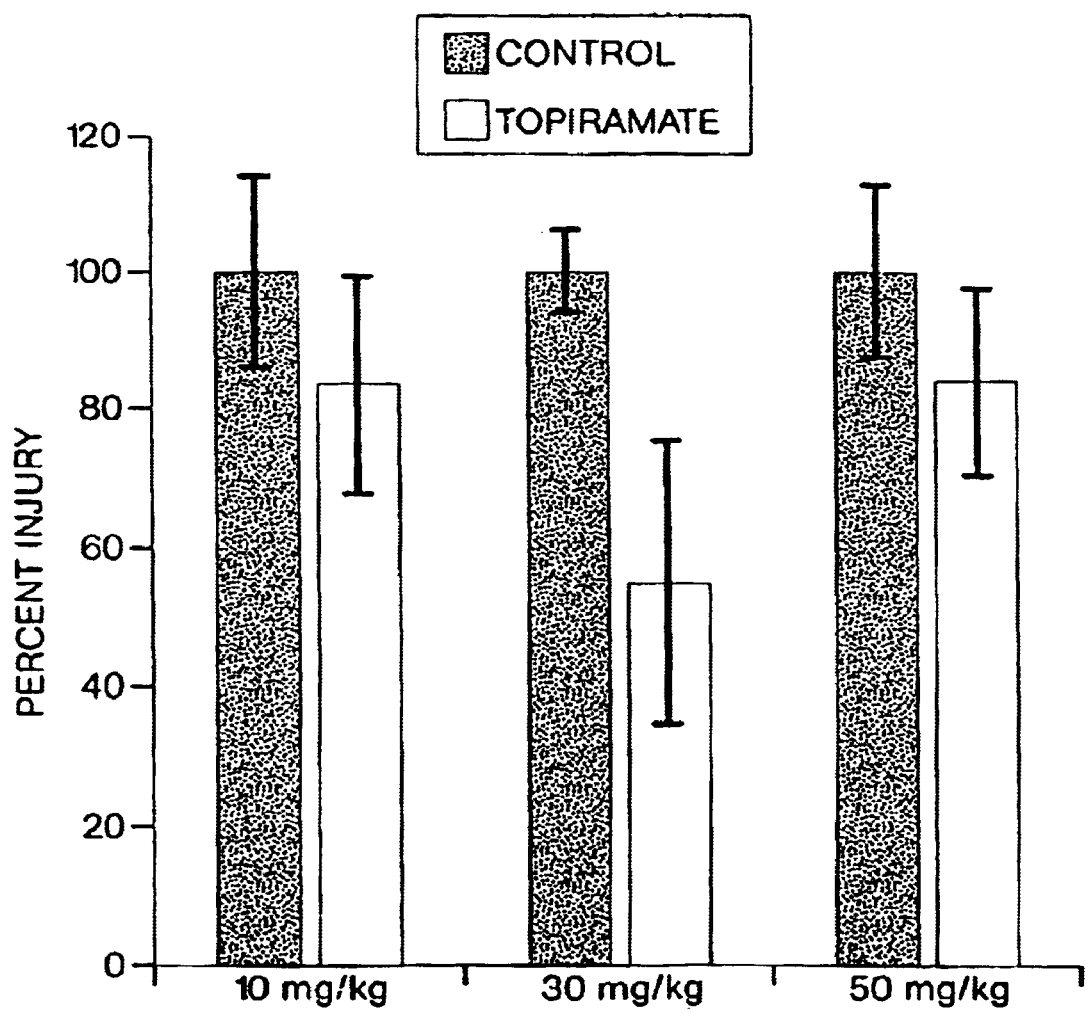
Figure 4D:

Topiramate and NBQX Protect OL Precursor Cells from OGD- or KA-Induced Cell Death in vitro First, a comparison was performed to assess the efficacy of topiramate and the AMPA antagonist NBQX in protecting against kainate-induced excitotoxicity and oxygen-glucose deprivation (OGD)-induced cell death in OL precursor cultures. OGD has been previously shown to cause non-NMDA receptor-mediated ischemic cell death in a similar culture model (Fern and Moller, 2000). Routine characterization of the OL precursor cultures by immunochemical detection of the precursor marker, A2B5, and the astrocyte marker, GFAP, demonstrated that in typical cultures approximately 90% of the cells are OL precursors, with less than 5% astrocytes. OL precursor cultures were incubated with 0, 5, 10, 30, 50, 100 μM topiramate or NBQX then exposed to either 2-hr OGD or 300 μM kainate. Cell survival was assessed 24 hr later. Dose-response curves shown in FIG. 4 show that NBQX at ≥10 μM significantly reduced kainate (300 μM)-induced cell death, and at 50 μM was fully protective, whereas topiramate exerted significant protective effect at ≧30 μM and achieved approximately 70% of cell survival at 50–100 μM (FIG. 4A). Meanwhile, topiramate and NBQX similarly prevented OGD-induced OL death, and the protective effects of both were significant at ≧30 μM (p<0.05 by ANOVA-Tukey analysis, FIG. 4B).

Figure 4E:
Figure 4F:
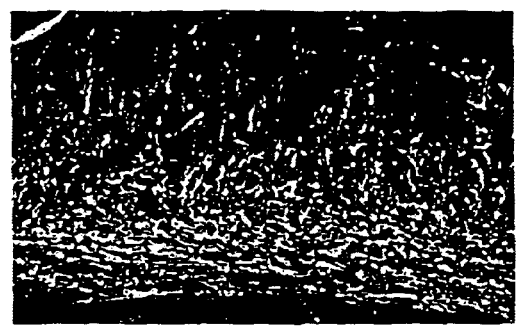
Figure 4G:
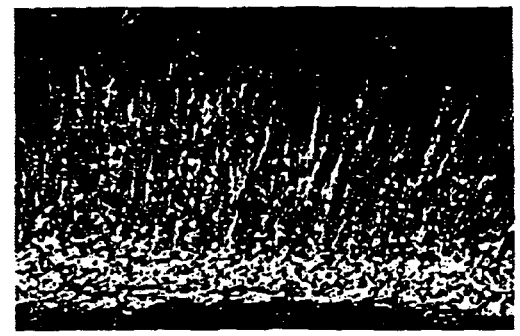
Figure 4H:
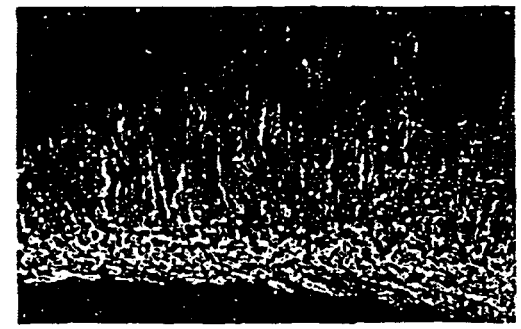

Topiramate Attenuates Loss of MBP in a Rodent Model of Selective White Matter Injury Given the similar protective effect of NBQX and topiramate on OGD-induced cell death in OL precursor cultures, as well as the efficacy the of NBQX on selective white matter injury in the rat model (Follett et al., 2000), an evaluation as to whether topiramate would attenuate selective white matter injury in vivo was performed. Each litter was divided and pups were treated with 10, 30 or 50 mg/kg of topiramate, or an equal volume of PBS, at the termination of hypoxia (1 hour at 6%, 1 hour after carotid ligation), with repeat doses every 12 hours for 48 hours. Untreated, this insult typically produces a selective, unilateral injury of sub-cortical white matter with relative sparing of the cortex (FIG. 4D), demonstrated most markedly by loss of myelin basic protein (MBP) staining ipsilateral to the ligation (FIG. 4E). As previously seen with NBQX, littermates treated with topiramate frequently showed a marked attenuation of the ipsilateral decrease in MBP staining 96 hours after the insult (FIG. 4G and FIG. 4H). A blinded, semi-quantitative analysis of MBP expression 96 hours after the hypoxia demonstrated significant attenuation of lesion severity in rats treated with 30 mg/kg of topiramate, as compared with vehicle-treated controls (FIG. 4C, p<0.01, Student's t-test with unequal variances). The resulting partial dose response curve evaluating 40 mg/kg (n=), 120 mg/kg (n=) and 200 mg/kg (n=), given as divided doses over 48 hours, shows maximal protective effect at 30 mg/kg/dose, with less efficacy at the lower dose and a question of possible toxicity at the higher dose. The clearance of topiramate in these immature pups is unknown and repetitive doses may cause increasing blood levels. Increased numbers of pups were necessary at higher and lower doses to allow for sufficient power to discard significance.

Figure 5A:
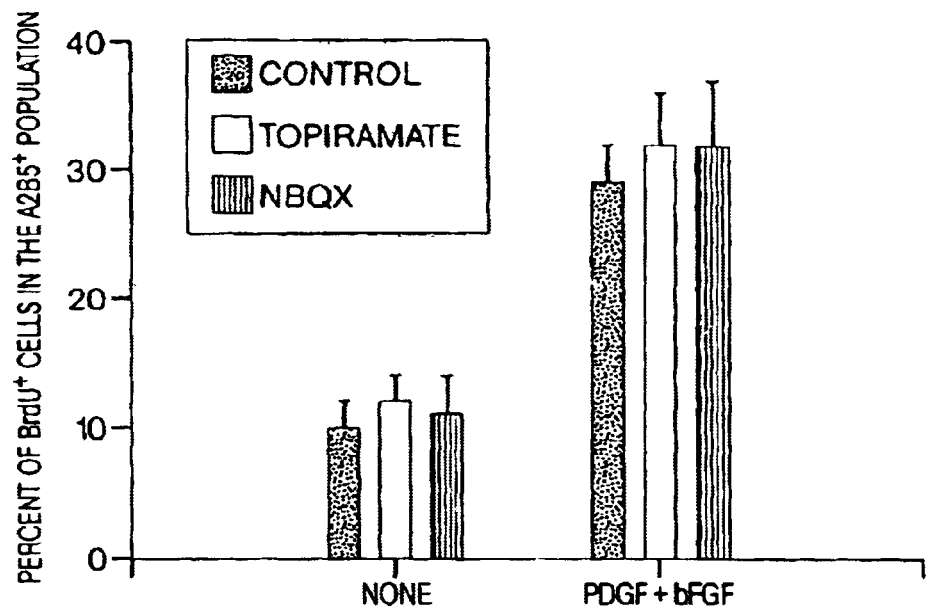
FIGS. 5A–5D demonstrate that NBQX and topiramate do not effect maturation or proliferation of OLs at protective doses.

OL Precursor Cell Proliferation and Maturation Unaffected by Topiramate or AMPA Antagonist NBQX in vitro Since AMPA/kainate antagonists have been shown to alter in maturation rates and proliferation in other in vitro systems (Gallo et al.,1996; Yuan et al., 1998), an evaluation of whether the protective effect of topiramate and NBQX on OL precursors was impacted by the action of these agents on cell proliferation and differentiation was performed. The proliferative capability of the cells was measured by the incorporation of the thymidine analog BrdU into DNA. Cells were double-immunostained with anti-BrdU and the OL precursor marker A2B5, and the percent of BrdU$^+$ cells in A2B5$^+$ populations (% BrdU$^+$/A2B5$^+$) was determined by counting of the A2B5$^+$ cells. Neither topiramate nor NBQX, as used in this protocol, altered the proliferative capability or the differentiation potential of the cells (FIG. 5A). OL precursors in this system have limited cell-intrinsic proliferative capability in the absence of mitogens, thus appropriate growth factors were used as positive controls. Cultures were exposed to the following: vehicle, PDGF+bFGF (each at 10 ng/ml), topiramate (30 μM), or NBQX (100 μM), representing doses protective against cell death. BrdU (10 μM) was added to the culture medium in all groups at 22 hours, 2 hours before termination of the experiment. A quantitative analysis was obtained by counting the number of BrdU$^+$ cells in the A2B5$^+$ population and calculating a percent. Data represents the mean±SEM of at least three independent experiments. All assays were performed in triplicate and a minimum of 1000 cells counted for each data point. Neither topiramate or NBQX altered the rate of BrdU incorporation (*p<0.001 vs. control), whereas PDGF and bFGF dramatically enhanced cell proliferation by approximately 3-fold.

The effect of these protocols on maturation was also assessed. Differentiation of the cultures in the absence or presence of topiramate (30 μM) or NBQX (100 μM) was monitored by cell morphology and the sequential emergence of a panel of OL stage-specific markers (A2B5, O4, O1, and MBP), following 0, 2, 6, and 10 days of maturation. The results indicated that cells treated with either topiramate or NBQX progressed along the OL lineage in a manner indistinguishable from the progression of the control cultures.

OL Proliferation and Maturation Unaffected by AMPA Antagonist Treatment Protocol in vivo No mitogenic or maturational effect were detected on the OL precursor cultures using the treatment protocol. However, as AMPA antagonists have been previously shown to effect proliferation and maturation of OLs in other systems (Gallo et al., 1996; Yuan et al., 1998), and given the protective effect of topiramate on hypoxic/ischemic white matter injury in vivo, an investigation as to whether topiramate, given as in the protective protocol, induced either proliferative or maturational changes in developing white matter, was performed. Either would have important implications for both the mechanism of protection as well as the potential safety of the treatment protocol to the developing brain.

Figure 5B:
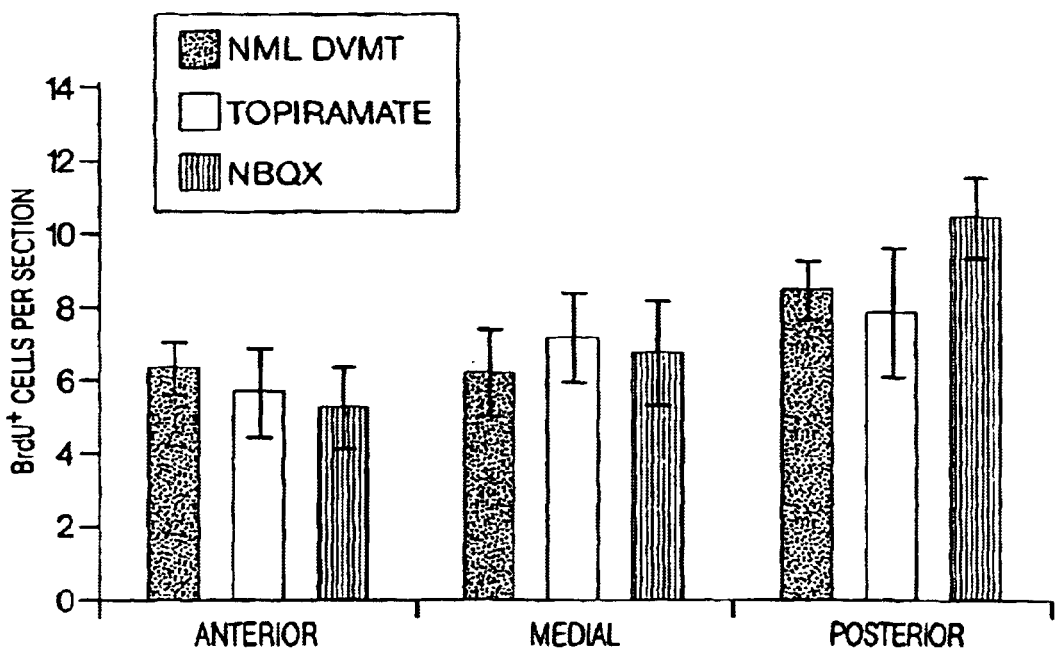
Figure 5C:
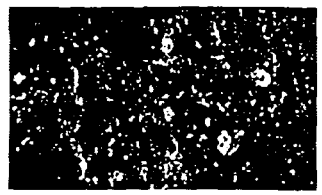
Figure 5D:
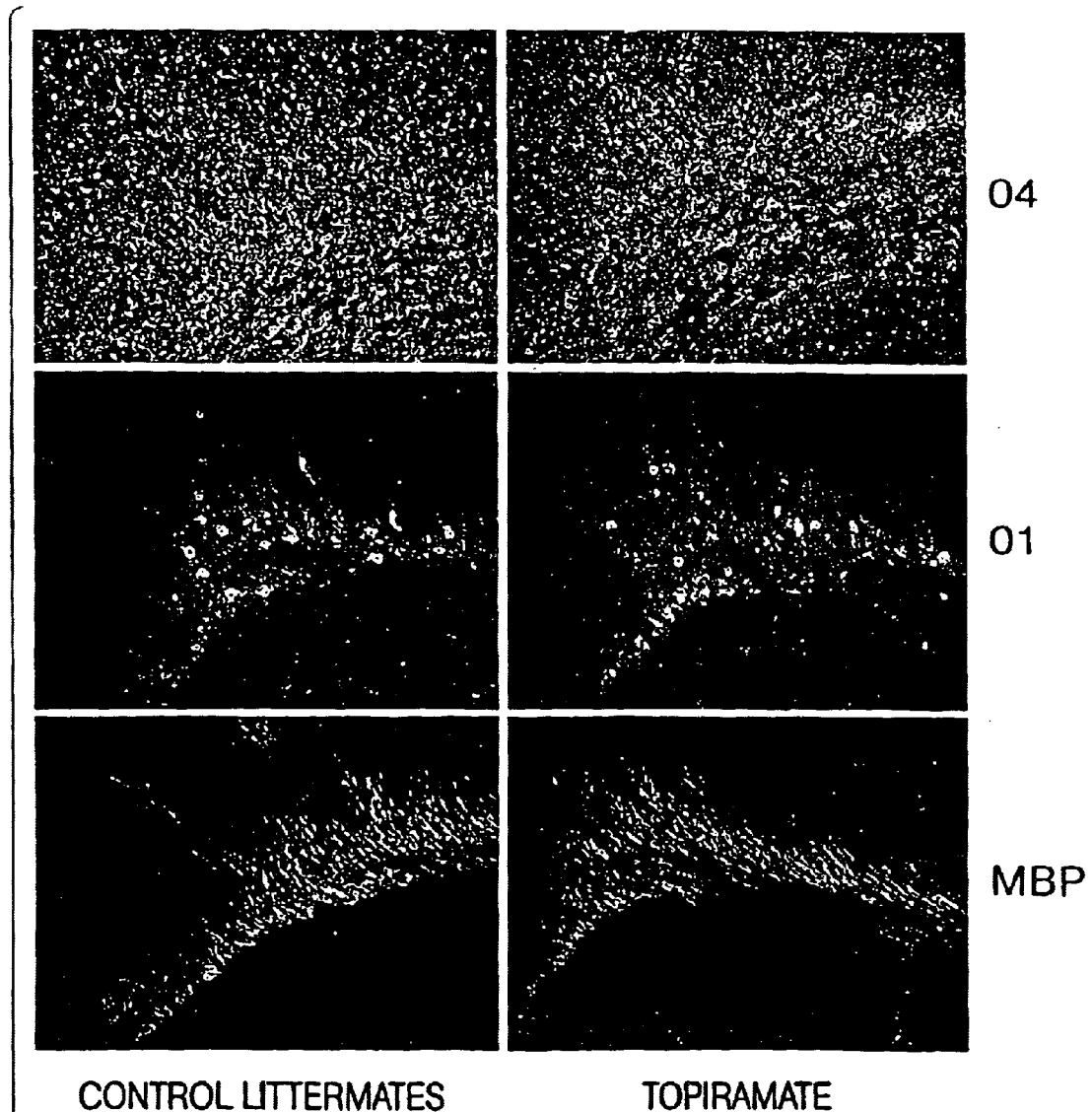

Litters were divided and pups received 4 injections, one every 12 hours for 48 hours at P7 and P8, of either vehicle (n=6), 30 mg/kg topiramate (n=7) or 20 mg/kg NBQX (n=7). These protocols are identical to those shown to be protective following hypoxia/ischemia except these animals received no insult. Concurrently, all pups received 120 mg/kg BrdU, also every 12 hours for 48 hours. At the completion of 48 hours the animals were sacrificed and the number of BrdU labeled, O4+ OLs present in the subcortical white matter of coronal sections (n=20/group) were counted (FIG. 5B). Sections were divided into anterior, containing anterior commissure, medial, containing dorsal hippocampus, and posterior, containing thalmus and ventral hippocampus for analysis in order not to mask anterior to posterior effects of maturational variability or differences in white matter volume. No difference in the number of proliferating OLs was detected between the groups (FIG. 5C, error bars demonstrate standard deviation). Furthermore, qualitative analysis of white matter by immunohistostaining for OL stage-specific markers O4, O1 and MBP was carried out in serial sections of the same animals evaluated above. No qualitative difference in maturation was seen at P9 (FIG. 5D) or at P11. FIG. 5D depicts high power image of O1 (red) and bisbenzamide, demonstrating immature OLs.

Figure 6A:
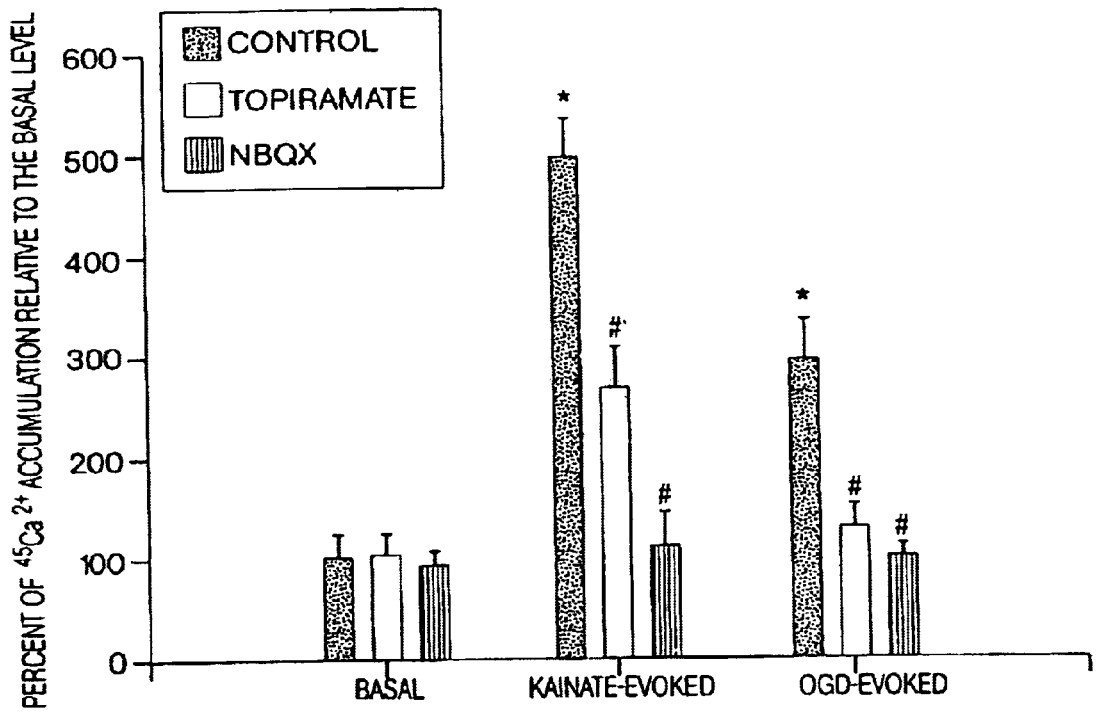
FIGS. 6A–6E demonstrate that topiramate blocks calcium uptake in OL precursors.

Topiramate and NBQX Prevent KA or OGD-Evoked $^{45}Ca^{2+}$ Influx to Oligodendrocyte Precursor Cells To gain further insight into the mechanisms of the protective effect of topiramate and NBQX, kainate- or OGD-evoked calcium accumulation in oligodendrocyte precursor cells was investigated. Cultures were either not treated or given NBQX (100 μM) or topiramate (30 μM), together with $^{45}CaCl_2$ (8 μCi/ml), before adding kainate (300 μM) or after exposure to OGD for 2 hr. $^{45}Ca^{2+}$ uptake was measured after 10 minutes. As shown in FIG. 6A, topiramate partially prevented and NBQX completely blocked kainate-evoked $Ca^{2+}$ entry, while both of the agents fully prevented OGD-induced $Ca^{2+}$ accumulation (*p<0.001 vs. the basal level; #p<0.001 vs. the absence of topiramate or NBQX).

Calcium Uptake via GluRs is Blocked by NBQX and Topiramate in situ

Figure 6B:
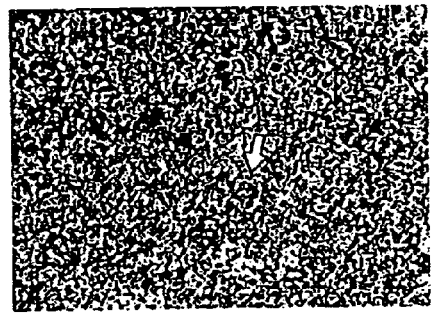
Figure 6C:
Figure 6D:
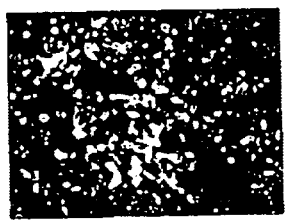
Figure 6E:
Figure 6F:
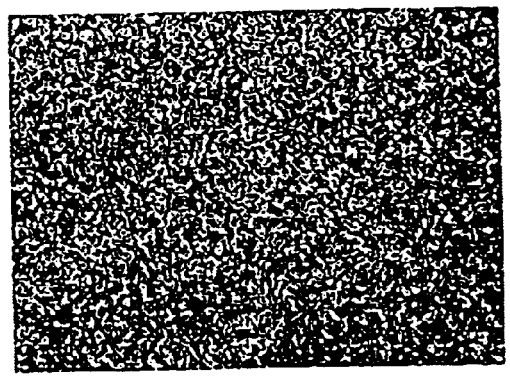
Figure 6G:
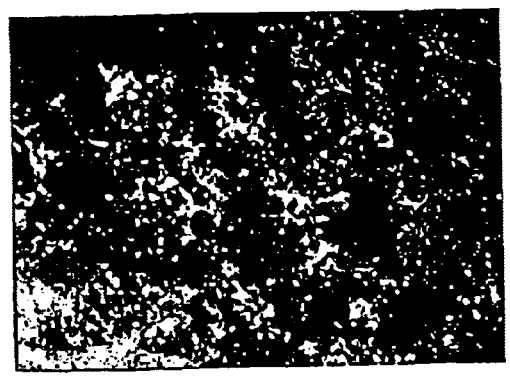
Figure 7A:
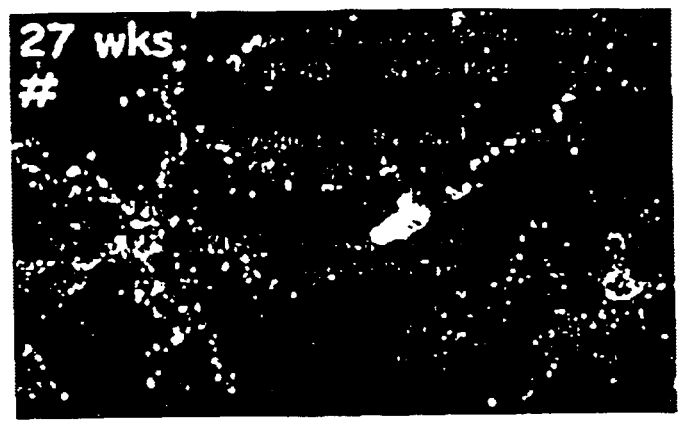
FIG. 7A depicts a section of human white matter immunocytochemically labeled with an antibody to the O4 antigen for oligodendrocyte precursor cells.
Figure 7B:
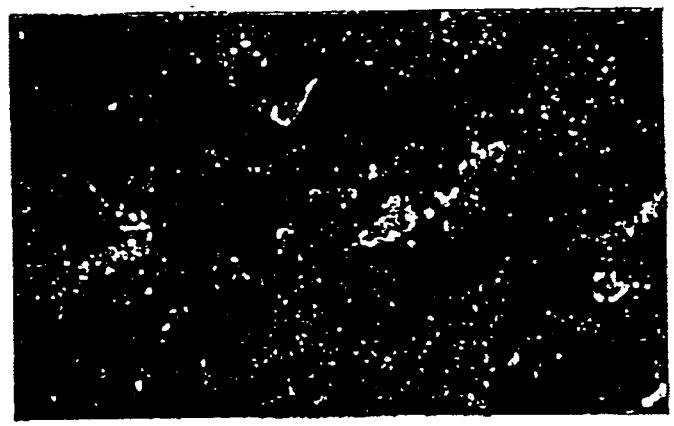
FIG. 7B depicts human white matter, which is the same section as Panel A, immunocytochemically labeled with antibody to the GluR4 subunit protein.
Figure 7C:
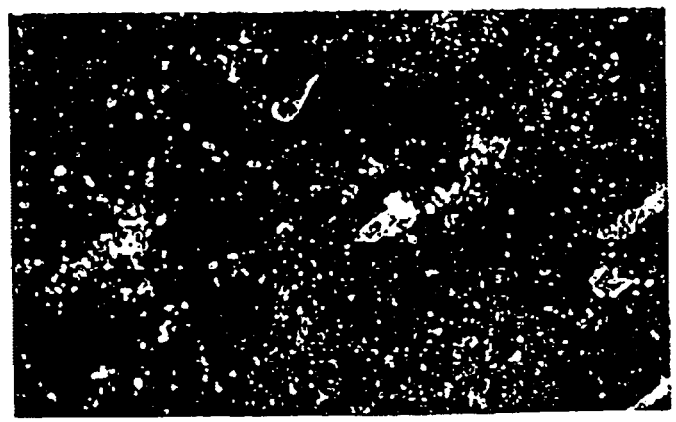
FIG. 7C depicts an overlay of the double labeling from Panels A and B showing co-localization of O4 antibody and GluR4 antibody (yellow). Panel C reveals the presence the glutamate receptors on oligodendrocyte precursor cells in human white matter.

As calcium has been show to mediate excitotoxicity, and calcium permeable AMPA receptors have been shown to be present in other brain areas during maturation, the immature white matter in the brain slice at P7 for the presence of calcium permeable AMPA/kainate receptors and the effect of topiramate on calcium permeability were evaluated. Cortical slices were assessed for the presence of AMPA induced cobalt uptake in coronal slices from P7 rats. Cobalt is a divalent cation that substitutes for calcium via GluR mediated channels, but blocks, and thus does not enter, via voltage-gated calcium channels. Immature OLs in periclalosal white matter at P7 show consistent cobalt uptake following 20 minute incubation with 100 $\mu$M AMPA, 100 $\mu$M MK-801 in low $Ca^{2+}$, cobalt containing rat ACSF (FIG. 6B). Cobalt-containing white matter cells were identified as OL precursors by immunolabeling with O4 surface antigen (FIG. 6C and FIG. 6D). Sections were labeled with O4 prior to the cobalt-up-take experiments, utilizing the feature of O4 as an external antigen that allows it to be used on live cells. All experimental sections were also co-incubated with MK-801 to block any NMDA receptor activity. Uptake was effectively blocked by either 100 $\mu$M NBQX (FIG. 6E), or by 50 $\mu$M topiramate (FIG. 6F and FIG. 6G), with a partial effect seen with 10 $\mu$M topiramate. ICC with vital marker for O4 was used to identify cells as pre-OLs (FIG. 6D and FIG. 6G).

Discussion

It has been previously demonstrated that a role for excitotoxicity in the increased vulnerability of white matter to hypoxic/ischemic injury at P6/7 is correlated with maturational differences in GluR receptor expression in developing OLs, and consistent with results of others (Follett et al., 2000; Fern and Moller, 2000; Itoh et al., 2002). Example 3 reinforces this finding and further suggests that the approved drug topiramate may be useful in the attenuation of that injury. A dose-dependent attenuation of OL cell death and selective white matter injury with topiramate has been demonstrated. In addition, there is a lack of modulation on OL proliferation and maturation and white matter development with doses of topiramate effective for treatment, supporting the hypothesis that developmental influences are not responsible for the protective effect. Moreover, the tendency of these vulnerable OLs to exhibit AMPA/kainate invoked calcium uptake via GluR channels is blocked by both NBQX and topiramate, consistent with the currently hypothesized mechanism of action of these agents. And finally, the potential relevance of these in vivo and in vitro findings has been demonstrated by showing the presence of AMPA receptors in human tissue at the age most vulnerable to white matter injury (Kinney and Back, 1998). These findings confirm that calciummediated excitotoxicity is a contributing factor in age-dependent, selective white matter injury, suggesting an important role for AMPA antagonists in age-dependent therapeutic strategies for PVL, and a significant role for topiramate in the prevention of this devastating condition.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for treating periventricular leukomalacia (PVL), mental retardation, and/or neonatal stroke in a human subject comprising administering to the human subject topiramate and a pharmaceutically acceptable carrier such that PVL, mental retardation, and/or neonatal stroke is treated.

2. The method of claim 1, wherein said human subject is a neonate.

3. A method for treating PVL, mental retardation, and/or stroke in a human fetus comprising administering to a pregnant mother topiramate and a pharmaceutically acceptable carrier such that PVL, mental retardation, and/or stroke is treated in the fetus.

4. A method for treating grey and/or white matter injury in the brain of a perinatal subject comprising administering to the perinatal subject topiramate and a pharmaceutically acceptable carrier such that grey and/or white matter injury in the brain is treated.

5. A method for treating grey and/or white matter injury in the brain of a fetal subject comprising administering to a pregnant mother topiramate and a pharmaceutically acceptable carrier such that grey and/or white matter injury in the brain of the fetal subject is treated.

* * * * *